(12) United States Patent
Majeed et al.

(10) Patent No.: US 9,458,075 B1
(45) Date of Patent: Oct. 4, 2016

(54) PROCESS FOR THE MANUFACTURE OF 3'-HYDROXY PTEROSTILBENE

(71) Applicants: Muhammed Majeed, Edison, NJ (US); Kalyanam Nagabhushanam, East Windsor, NJ (US); Savita S Ganjihal, Bangalore (IN)

(72) Inventors: Muhammed Majeed, Edison, NJ (US); Kalyanam Nagabhushanam, East Windsor, NJ (US); Savita S Ganjihal, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 14/718,088

(22) Filed: May 21, 2015

(51) Int. Cl.
*C07C 41/26* (2006.01)
*C07C 45/00* (2006.01)

(52) U.S. Cl.
CPC .............. *C07C 41/26* (2013.01); *C07C 45/00* (2013.01)

(58) Field of Classification Search
CPC ................................ C07C 41/26; C07C 45/00
See application file for complete search history.

(56) References Cited

U.S. PATENT DOCUMENTS

2007/0276172 A1* 11/2007 Sinha ...................... C07C 41/30
585/428
2012/0165567 A1* 6/2012 Sharma ................ C07D 317/54
562/465

FOREIGN PATENT DOCUMENTS

CN 104387246 A * 3/2015 ............. C07C 41/26

* cited by examiner

*Primary Examiner* — Rosalynd Keys

(57) ABSTRACT

The invention discloses high yielding synthetic process for 3'-hydroxy pterostilbene.

2 Claims, 6 Drawing Sheets

FIG. 2

PROCESS FOR THE MANUFACTURE OF 3'-HYDROXY PTEROSTILBENE

BACKGROUND OF THE INVENTION

1. Field of Invention

The present invention in general relates to 3'-hydroxy pterostilbene (3'-HPT). More specifically, the present invention relates to the synthesis of 3'-hydroxy pterostilbene.

2. Description of Prior Art

The medical significance of 3'-hydroxy pterostilbene as an apoptosis inducing agent as compared to trans-resveratrol and piceatannol is well documented (M. Tolomeo et al./The International Journal of Biochemistry & Cell Biology 37 (2005) 1709-1726). 3'-HPT has also been documented to be a more potent anti-cancer agent than pterostilbene (PLoS ONE 9(11), 2014, e111814).

Synthetic schemes for 3'-hydroxy pterostilbene with low yields have also been documented in prior art. The important ones are, A. Wittig Reaction based synthesis of 4-[2-(3,5-Dimethoxyphenyl)ethenyl]-1,2-benzenediol (3'-hydroxy pterostilbene) with an overall yield of 33% (Somepalli VENKATESHWARULU et al in *Biosci. Biotechnol. Biochem.*, 67 (11), 2463-2466, 2003). In this prior art reference, several technical disadvantages are noted.
  a) The Wittig condensation uses n-butyl lithium which is very difficult to handle in industrial synthetic schemes;
  b) The Wittig condensation also produces cis and trans forms of the stilbenes and it is only the trans form that may be effectively de-benzylated to form 3'-hydroxy pterostilbene. Obtaining the trans stilbene by column chromatography has been contemplated. However, this is not feasible in industrial production. Further, the conversion of cis to trans stilbene uses iodine which is very expensive to use in an industrial scale and the conversion could again produce both cis and trans stilbenes.

B. The condensation of 3,5-dimethoxyphosphonium bromide with 3',4'-di(tert-butyldimethylsilyloxy)benzaldehyde to get a mixture of cis and trans stilbenes and followed by the deprotection of isomeric forms to yield 25% 3'-hydroxy pterostilbene (Journal of Medicinal Chemistry, 2003, 46, 3646-3554). In this prior art, the technical disadvantages include,
  a) The starting reactant 3',4'-di(tert-butyldimethylsilyloxy)benzaldehyde represents a bulky group to handle in an industrial set up; and
  b) The formation of cis and trans isomers of the stilbene reduces the yield of desired trans isomer.

Alternatives to the aforementioned low yield and industrially non-feasible technical processes for the synthesis of 3'-hydroxy pterostilbene form the primary objective of the present invention. Accordingly, it is the primary objective of the present invention is disclose a industrially viable, high yielding synthetic scheme for 3'-hydroxy pterostilbene. The present invention fulfills this objective and provided further related advantages.

SUMMARY OF THE INVENTION

Disclosed are novel synthetic schemes for the production of 3'-hydroxy pterostilbene. The present invention provides the following advantages.

1. The invention uses starting material pterostilbene which is commercially available in bulk quantities or can be prepared by well documented synthetic schemes.
2. The invention is (a) cost effective; (b) an example of a viable chemical synthetic scheme that uses favorable reactants and reagents; (c) industrially scalable involving minimal reaction steps; and (d) economically viable by producing high yield (60-70%) of 3'-hydroxy pterostilbene.

Other features and advantages of the present invention will become apparent from the following more detailed description, taken in conjunction with the accompanying images, which illustrate, by way of example, the principle of the invention.

DETAILED DESCRIPTION OF THE MOST PREFERRED EMBODIMENT

Figure 1:
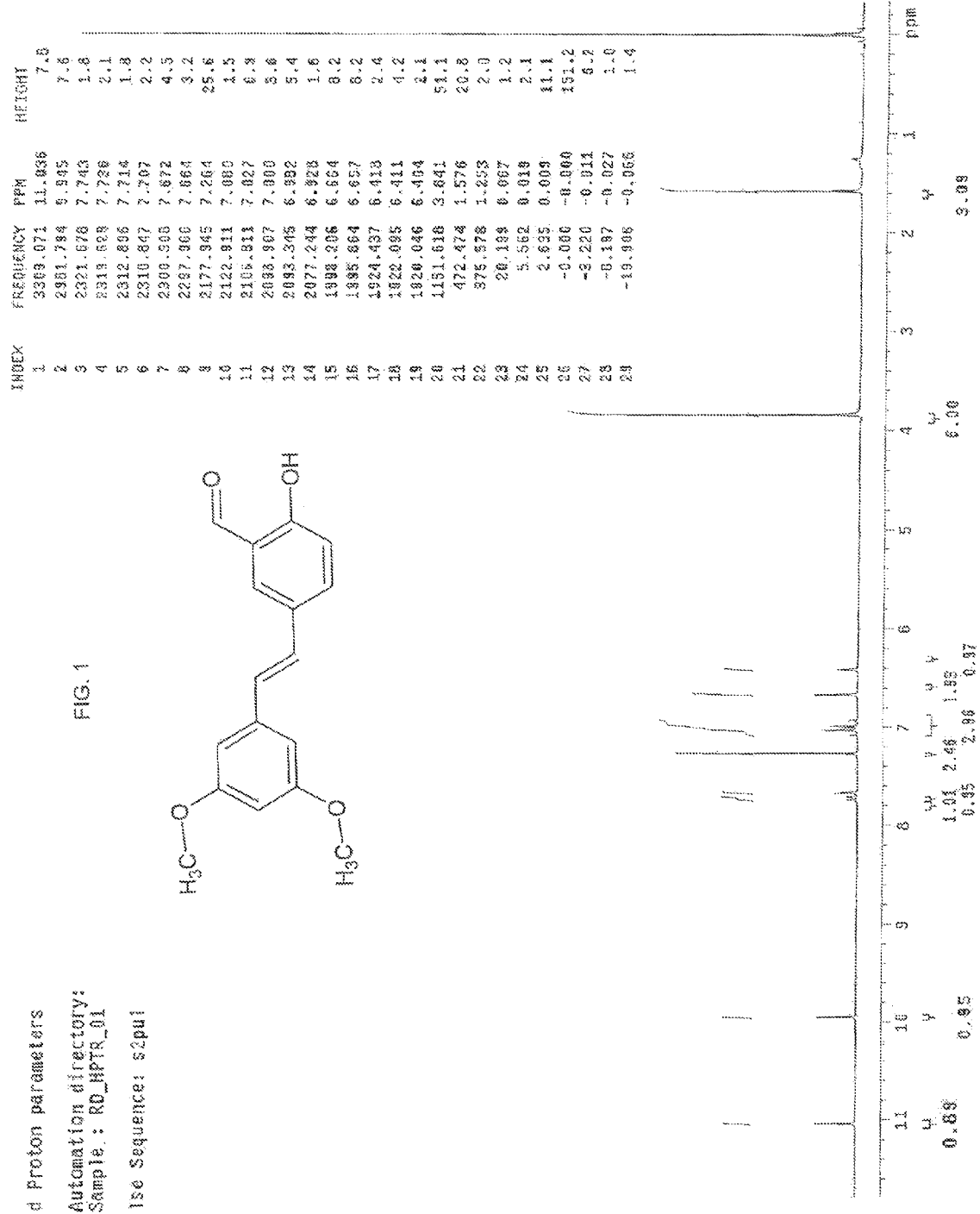
FIGS. 1a and 1b shows the NMR of 3'-formyl pterostilbene showing separate peaks 3.841 (6H, s, 3,5-OCH3), 6.404 (1H, t, J=2.1 Hz, H-4), 6.657 (2H, d, J=2.1 Hz, H-2,6), 6.928 (1H, d, 16.2 Hz, β-H), 7.080 (1H, d, J=16.0 Hz, α-H), 7.00 (1H, d, J=8.1 Hz, H-5'), 7.672 (1H, d, J=2.4 Hz, H-2), 7.743 (1H, dd, J=8.7 Hz, 2.1 Hz, H-6'), 9.945 (1H, s, H—CHO), 11.03 (1H, s, H—OH)
Figure 1A:
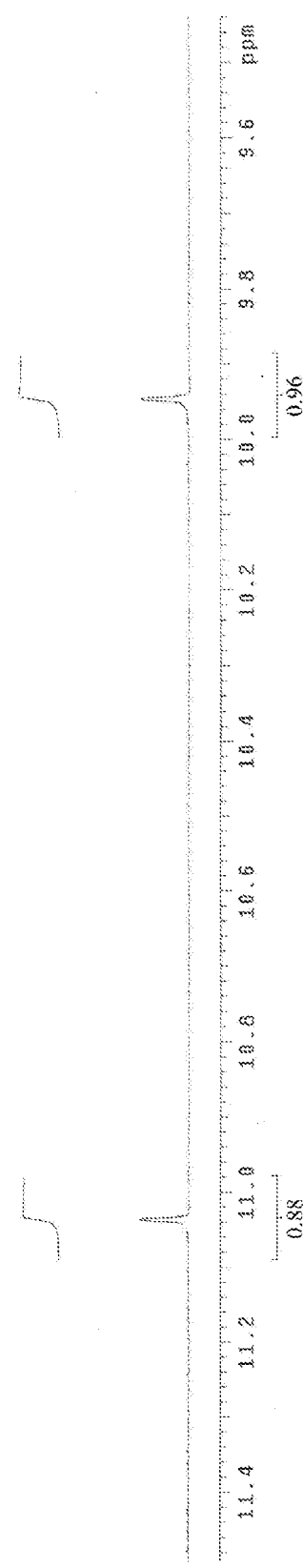
Figure 1B:
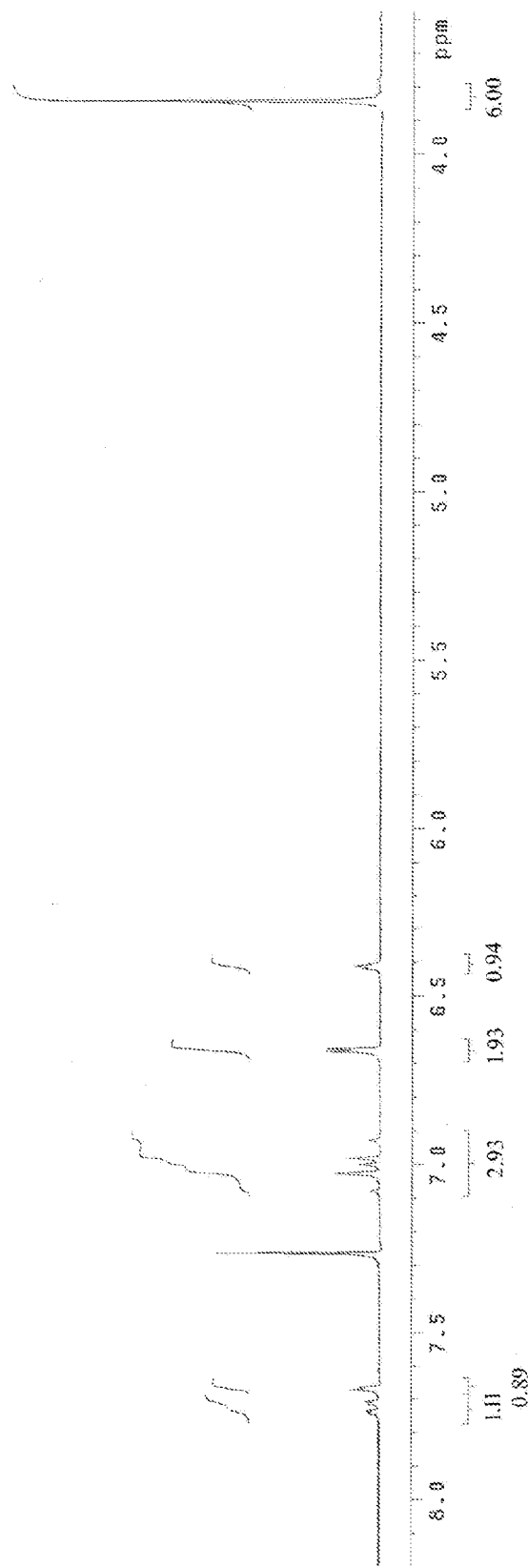
Figure 2A:
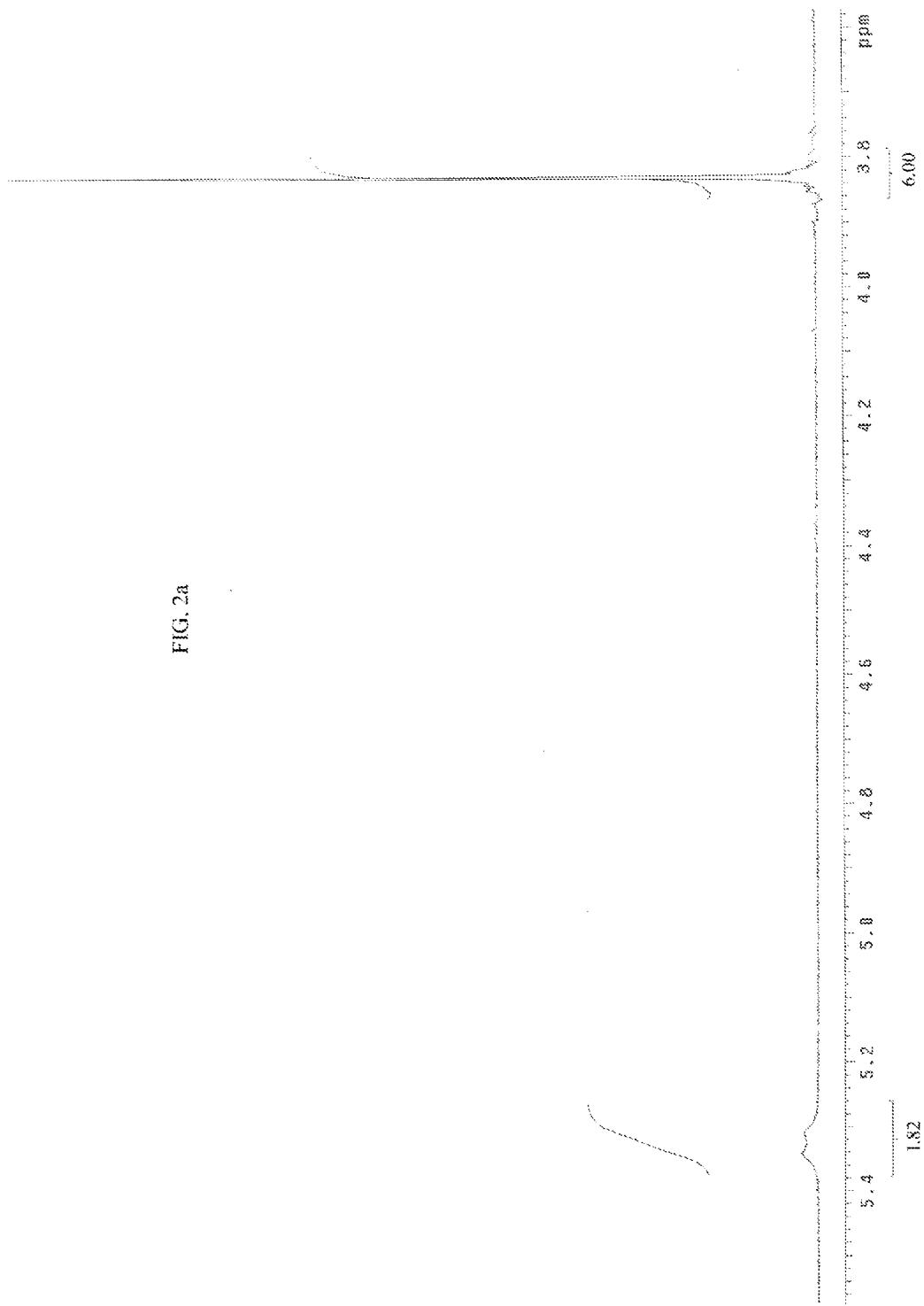
FIGS. 2a and 2b shows the NMR of 3'-hydroxy pterostilbene showing separate peaks 3.853 (6H, s, 3,5-OCH3), 6.389 (1H, t, J=2.3 Hz, H-4), 6.640 (2H, d, J=2.3 Hz, H-2,6), 5.311 (1H, s, 4'-OH), 5.342 (1H, s, 3'-H), 6.866 (1H, d, j=8.2 Hz, 5'-H), 6.878 (1H, d, J=16.4 Hz, α-H), 6.939 (1H, d, J=16.1 Hz, β-H) 6.951 (1H, dd, J=8.2 Hz, 2.0 Hz, H-6'), 7.261 (1H, d, J=2.0 Hz, H-2')
Figure 2B:
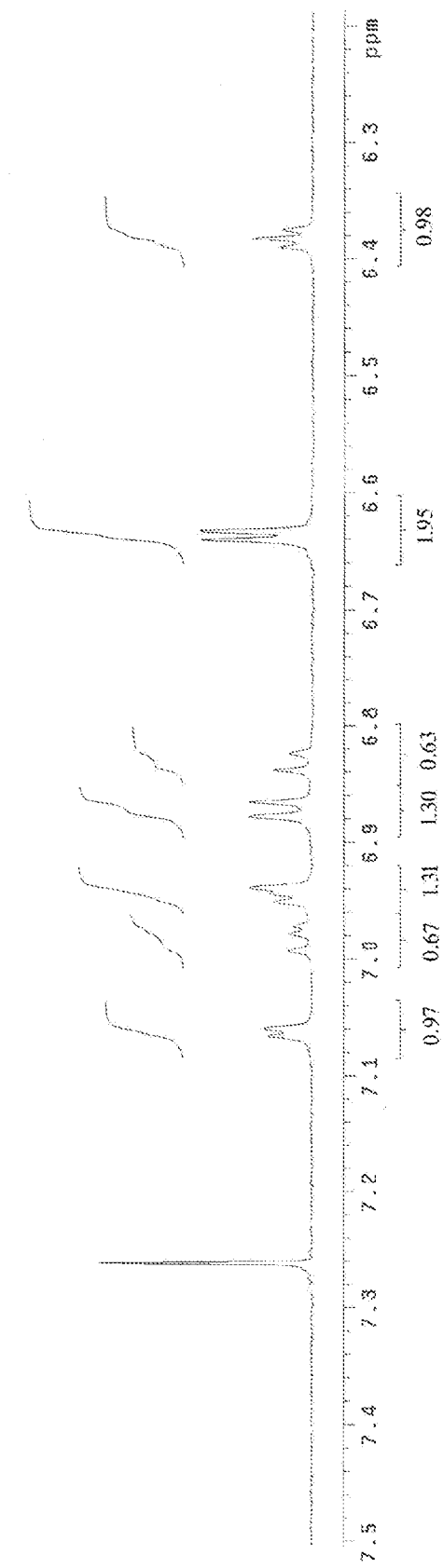

In the most preferred embodiment, the present invention relates to a novel process for the synthesis of 3'-hydroxy pterostilbene, said process comprising steps of:
  a) Orthoformylation of pterostilbene by using anhydrous magnesium chloride, triethylamine and paraformaldehyde to obtain 3'-formyl pterostilbene (Illustrated herein below as Step 1); and

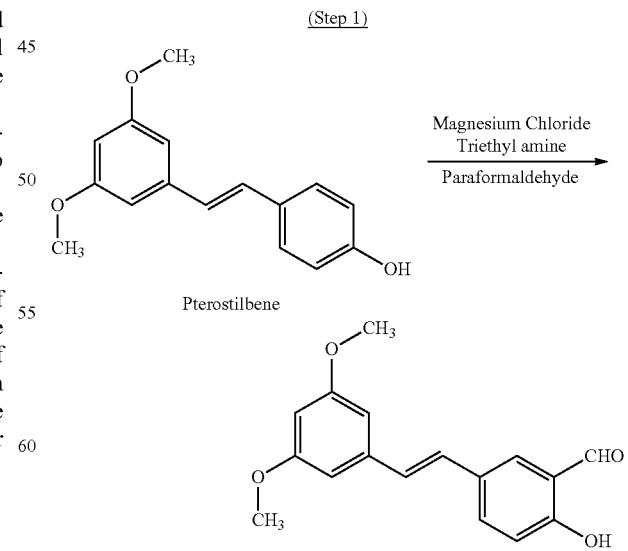

b) Subjecting 3'-formyl pterostilbene obtained in Step 1 to Dakin oxidation using hydrogen peroxide in sodium hydroxide to form Y-hydroxy pterostilbene (illustrated herein below as Step 2).

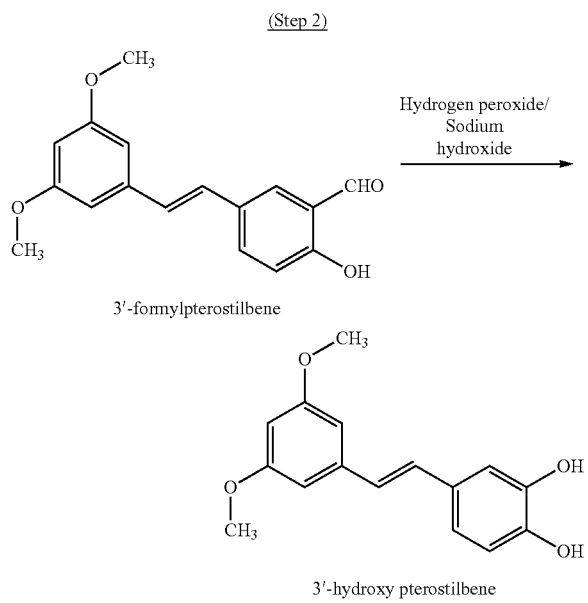

In another most preferred embodiment, the present invention also relates to the process for the synthesis of 3'-hydroxy pterostilbene, said process comprising step of ortho hydroxylating pterostilbene using 2-Iodoxy benzoic acid followed by insitu reduction using Sodium dithionite to obtain 3'-hydroxy pterostilbene (illustrated herein below as Step 3).

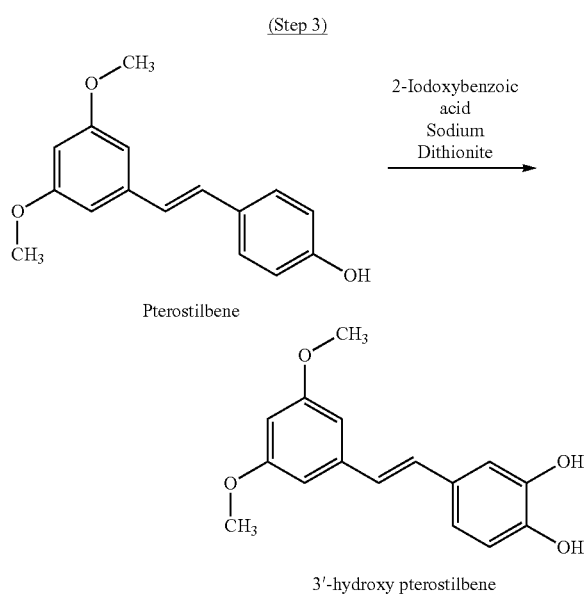

The following sections of the specification consist of illustrative examples of the most preferred embodiments of the present invention Example 1

Preparation of 3'-Formyl Pterostilbene

To a solution of pterostilbene (100 g, 0.3906 mol, 1 eq) in acetonitrile (1.0 liter), paraformaldehyde (94 g, 3.125 mol, 8 eq), triethylamine (163 ml, 1.1718 mol, 3 eq) and anhydrous magnesium chloride (111 g, 1.1718 mol, 3 eq) were added at room temperature. The solution was stirred for 5-6 hours at reflux temperature and monitored by TLC. When the substrates disappeared, water was added and acidified with dil HCl. Reaction mixtures were extracted with dichloromethane. Organic phases were washed with water and then dried on sodium sulfate. The organic solvent was evaporated under reduced pressure obtaining crude product, which was stirred with isopropyl alcohol at 0° C. to obtain pure product as solid (Yield: 90 g).

Example 2

Preparation of 3'-Hydroxypterostilbene

To a solution of 3'-formyl pterostilbene (90 g, 0.317 mol, 1 eq) in THF (810 ml) and water (90 ml), hydrogen peroxide (65 ml. 0.7130 mol, 2.25 eq), solution of sodium hydroxide (21 g, 0.412 mol, 1.3 eq) was added at room temperature through dropping funnel. The solution was stirred at room temperature for 1 hour and monitored by TLC. When the substrates disappeared, reaction mixture was quenched with water, adjusted the pH to neutral with dil HCl. Reaction mixtures were extracted with dichloromethane. Organic phases were washed with sodium thiosulfate, water and then dried on sodium sulfate. The organic layer was evaporated under reduced pressure obtaining crude product, which was crystallized to obtain pure product as solid (Yield: 62 g).

Example 3

Preparation of 3'-Hydroxy Pterostilbene

To a solution of pterostilbene (10 g) in DMSO (50 ml) IBX was added (1.2 eq). The reaction mixture was stirred at room temperature and monitored by TLC. When the substrates disappeared, reaction mixture quenched with water and sodium dithionite solution. Product extracted with ethylacetate. The organic phases were washed with a solution of sodium bicarbonate and dried on sodium sulfate. The organic layer was evaporated under reduced pressure obtaining crude product which was purified by column chromatography on silica gel (Yield: 2.5 g). It may be noted that the orthohydroxylation of pterostilbene using IBX followed by in situ sodium dithionite reduction resulted in only 25% yield of 3'-hydroxypterostilbene. Nevertheless, the method was technically advantageous being a single step, green chemistry based synthesis.

The aforesaid examples are provided to enable one skilled in the art to practice the invention. The examples merely illustrate the general process of the invention. However, the included examples are not intended in any way to limit the scope of the present invention.

We claim:
1. A process for the synthesis of 3'-hydroxy pterostilbene, said process comprising steps of:
   a) Orthoformylation of pterostilbene by using anhydrous magnesium chloride, triethylamine and paraformaldehyde to obtain 3'-formyl pterostilbene; and b) Subjecting 3'-formyl pterostilbene obtained in step (a) to Dakin oxidation using hydrogen peroxide in sodium hydroxide to form 3'-hydroxy pterostilbene.

2. The process as claimed in claim 1, wherein said process comprises steps of:
 a. Adding at room temperature, paraformaldehyde, triethylamine and anhydrous magnesium chloride to a solution of pterostilbene in acetonitrile;
 b. Stirring the solution of step (a) at reflux temperature and monitoring using thin layer chromatography (TLC);
 c. Upon disappearance of substrates, adding to step b, water and further acidifying with dilute hydrochloric acid;
 d. Extracting the reaction mixtures of step c with dichloromethane;
 e. Washing the organic phases of the extract of step d with water and further drying on sodium sulfate;
 f. Evaporation of the extract of step e to remove organic solvents under reduced pressure to obtain crude 3'-formyl pterostilbene;
 g. Adding isopropyl alcohol (IPA) to crude 3'-formyl pterostilbene of step f to obtain pure 3'-formyl pterostilbene as solid;
 h. Adding solution of sodium hydroxide at room temperature to a solution of 3'-formyl pterostilbene and hydrogen peroxide from step g in THF and water;
 i. Stirring the solution of step h at room temperature for 1 hour and monitoring the reaction by TLC;
 j. Upon disappearance of substrates, adding to step i, water and further acidifying with dilute hydrochloric acid;
 k. Extracting the reaction mixtures of step j with dichloromethane;
 l. Washing the organic phases of the extract of step k with sodium thiosulphate, water and further drying on sodium sulphate;
 m. Evaporation of the extract of step l to remove organic solvents under reduced pressure to obtain crude 3'-hydroxypterostilbene; and
 n. Crystallizing crude 3'-hydroxypterostilbene of step m to obtain solid final product.

\* \* \* \* \*